(12) United States Patent
Korenkiewicz (10) Patent No.: US 10,676,623 B2
(45) Date of Patent: Jun. 9, 2020

(54) WATERBORNE LATEX COATING COMPOSITIONS WITH VISCOSITY-MODIFYING COALESCENCE AIDS

(71) Applicant: Valspar Sourcing, Inc., Minneapolis, MN (US)

(72) Inventor: Stephen Korenkiewicz, Lake Zurich, IL (US)

(73) Assignee: Valspar Sourcing, Inc., Minneapolis, MN (US)

( * ) Notice: Subject to any disclaimer, the term of this patent is extended or adjusted under 35 U.S.C. 154(b) by 50 days.

(21) Appl. No.: 15/782,701

(22) Filed: Oct. 12, 2017

(65) Prior Publication Data

US 2018/0105706 A1 Apr. 19, 2018

Related U.S. Application Data (60) Provisional application No. 62/408,590, filed on Oct. 14, 2016.

(51) Int. Cl.

| | | |
|---|---|---|
| *C09D 7/00* | (2018.01) | |
| *C09D 121/02* | (2006.01) | |
| *C09D 5/02* | (2006.01) | |
| *C09D 133/08* | (2006.01) | |
| *C09D 133/10* | (2006.01) | |
| *C09D 7/43* | (2018.01) | |
| *C09D 125/14* | (2006.01) | |
| *C08L 25/14* | (2006.01) | |
| *C07C 305/04* | (2006.01) | |
| *C08L 25/08* | (2006.01) | |
| *C08L 71/00* | (2006.01) | |
| *C08L 75/04* | (2006.01) | |

(52) U.S. Cl.
CPC .............. *C09D 7/43* (2018.01); *C09D 5/024* (2013.01); *C09D 5/027* (2013.01); *C09D 121/02* (2013.01); *C09D 125/14* (2013.01); *C09D 133/08* (2013.01); *C09D 133/10* (2013.01); *C07C 305/04* (2013.01); *C08L 25/08* (2013.01); *C08L 25/14* (2013.01); *C08L 71/00* (2013.01); *C08L 75/04* (2013.01)

(58) Field of Classification Search
CPC .......... C09D 7/00; C09D 5/02; C09D 121/02; C09D 133/08; C09D 133/10
USPC ......................................................... 524/156
See application file for complete search history.

(56) References Cited

U.S. PATENT DOCUMENTS

| | | | |
|---|---|---|---|
| 4,079,028 A | 3/1978 | Emmons et al. | |
| 4,155,892 A | 5/1979 | Emmons et al. | |
| 4,426,485 A | 1/1984 | Hoy et al. | |
| 4,782,109 A | 11/1988 | DuLaney et al. | |
| 5,574,127 A | 11/1996 | Sau | |
| 2007/0298270 A1* | 12/2007 | Hazel .................. | B05D 7/14 428/469 |

FOREIGN PATENT DOCUMENTS

| | | | |
|---|---|---|---|
| EP | 1518904 | * | 3/2005 |
| EP | 1518904 A1 | | 3/2005 |
| EP | 2982701 | * | 2/2016 |
| EP | 2982701 A1 | | 2/2016 |
| WO | 2008150295 A1 | | 11/2008 |
| WO | 2009114684 A2 | | 9/2009 |

OTHER PUBLICATIONS

International Search Report and Written Opinion of International Application No. PCT/US2017/056563, dated Jan. 3, 2018, 12 pp.
Kostanselt, "Associative Polymer/Latex Dispersion Phase Diagrams II: HASE Thickeners," JCT Research, vol. 2, No. 6, Apr. 2005, 6 pp.
Kostansek., "Associative Polymer/Particle Dispersion Phase Diagrams III: Pigments," JCT Research, vol. 3, No. 3, Jul. 2006, 7 pp.
Kostansek., "Using Dispersion/Flocculation Phase Diagrams to Visualize Interactions of Associative Polymers, Latexes, and Surfactants," Journal of Coatings Technology, vol. 75, No. 940, May 2003, 8 pp.
International Preliminary Report on Patentability from International Application No. PCT/US2017/056563, dated Apr. 25, 2019, 7 pp.

* cited by examiner

*Primary Examiner* — Deve V Hall
(74) *Attorney, Agent, or Firm* — Shumaker & Sieffert P.A.

(57) ABSTRACT

A coating composition including about 5 wt % to about 70 wt % of a latex or a water-dispersible film forming polymer, based on the total weight of the coating composition, a surfactant present in the coating composition at 0.1% to about 1% on the continuous phase of the coating composition; a polymeric associative thickener present in the coating composition at about 0.1% to about 2% on the continuous phase of the coating composition; about 0.1 wt % to about 5 wt % a styrene acrylic resin, based on the total weight of the coating composition; and an aqueous diluent.

18 Claims, 4 Drawing Sheets

FIG. 1

Formula 1

WATERBORNE LATEX COATING COMPOSITIONS WITH VISCOSITY-MODIFYING COALESCENCE AIDS

CROSS REFERENCE TO RELATED APPLICATIONS

This application claims the benefit of U.S. Provisional Application No. 62/408,590, filed on Oct. 14, 2016, the entire contents of which are incorporated herein by reference.

BACKGROUND

Waterborne latex coating compositions include an aqueous dispersion of particles of a film-forming polymeric resin and optional pigment particles which, when applied to a substrate and dried to form a film, impart substrate hide, water resistance, and durability to the film. Dispersants, surfactants, solvents and thickeners can be added to the coating compositions to adjust the viscosity of the composition, maintain a uniform and stable aqueous dispersion of the pigments and film-forming resin particles, and to improve properties of the paint film.

Waterborne latex coating compositions with higher volume solids provide more film build when the paint dries, which leads to improved hiding and improved scrub resistance. High quality paints tend to have higher levels of an acrylic latex, which binds the film together. The combination of high solids and high resin content makes these higher quality paints very responsive to water-soluble or emulsifiable associative thickeners such as, for example, polyurethane associative thickeners, often referred to as hydrophobically modified ethylene oxide urethane rheology modifiers (HEUR) thickeners.

Associative thickening involves non-specific interactions of hydrophobic end groups of a thickener molecule both with themselves and with components of the coating such as, for example, latex, pigments and dispersants. The thickener produces a reversible, dynamic network of thickener molecules and other components of the coating. The thickening effect is caused by interactions of the hydrophobic end groups of the thickener with other components of the formulation.

Some precomposite latexes, such as those available from DOW under the trade designation EVOQUE, include functional groups that allow several precomposite latex particles to adsorb on to a dispersed pigment particle such as, for example, $TiO_2$, and act as spacers in the dry film to prevent flocculation of the individual $TiO_2$ particles as the water evaporates from the wet paint. The use of precomposite lattices like the EVOQUE resins can lead to even higher viscosity paints before thickeners are added due to the increased hydrodynamic volume of the $TiO_2$/EVOQUE latex composite.

To maintain KU viscosity in specification, low levels of HEUR thickeners are used, which can lead to bridge flocculated paint. Bridge flocculation occurs when a single thickener molecule is adsorbed on two different particles. This bridging effect can occur when there is more surface area available on the particles than associative species in the coating composition system (for example, thickeners, surfactants and dispersants). Bridge flocculated paints can show syneresis, poor flow and leveling.

SUMMARY

Figure 1:
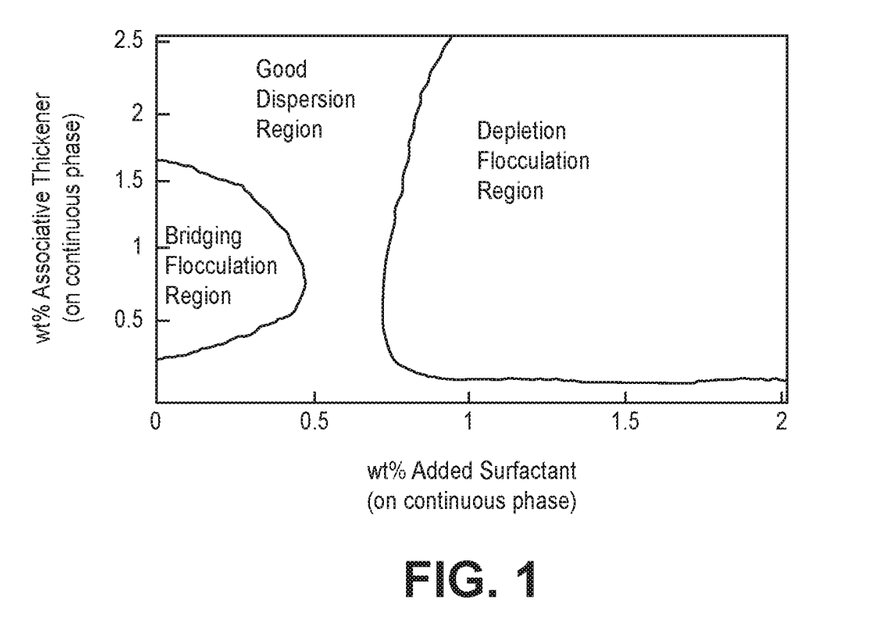
FIG. 1 is a plot of associative thickener concentration vs. surfactant concentration in a waterborne coating composition system.

FIG. 1 is a generalized dispersion phase diagram showing regions of bridge flocculation, good dispersion and depletion flocculation in a waterborne latex coating composition system including a HEUR associative thickener and a surfactant. In FIG. 1, HEUR associative thickener concentration is increasing on the vertical axis and surfactant concentration is increasing on the horizontal axis. The upper boundary of the bridging flocculation region is really a continuum of ever increasing floc sizes until a uniform dispersion is reached. This upper boundary is defined as the points at which individual flocs are no longer noticeable by microscopic inspection of the samples. The lower depletion flocculation boundary is the critical flocculation concentration (CFC) of the additive thickener, below which depletion flocculation does not occur. The polymeric colloidal latex particles in the latex coating composition can be removed from the bridging flocculation region by addition of HEUR thickener, and/or surfactant. The good dispersion region provides superior coatings properties. The latex coating composition system can enter the depletion flocculation region as increasing surfactant is added to the composition.

One method to fix bridge flocculation is to add sufficient surfactant to satisfy the unoccupied hydrophobic sites on the latex surface to move away from the bridge flocculated region of the dispersion phase diagram of FIG. 1. This high level of surfactant (for example, about 4 to about 8 pounds per 100 gal.) can lead to reduced stain resistance and reduced scrub resistance when the paint dries.

The present disclosure is based at least in part on the finding that a styrene acrylic resin can be used to reduce the KU viscosity of paint systems and reduce the likelihood of bridge flocculation like adding a surfactant, but do not decrease scrub resistance or stain removal in the dried paint film as would be expected from surfactant addition. In some embodiments, addition of viscosity modifying styrene acrylic resins lowered the KU viscosity, which allowed more associative thickener to be added without bridge flocculation, and the resulting paint composition had good flow and leveling and good application properties.

The additional associative thickener more substantially completely covers the surfaces on the colloidal polymeric latex particles and prevents bridge flocculation, while moving the waterborne latex coating composition into the good dispersion region of FIG. 1.

Addition of water soluble, non-film forming compounds like conventional surfactants to the coating composition to reduce viscosity can degrade properties of the paint film when the coating composition is applied on a substrate. However, compared to incorporation of a similar amount of a conventional surfactant, incorporating a viscosity modifying styrene acrylic resin into the coating composition to reduce viscosity and avoid bridge flocculation can improve paint film properties such as, for example, scrub resistance, stain resistance, block, and early water resistance.

In one aspect, the present disclosure is directed to a coating composition including about 5 wt % to about 70 wt % of a latex or a water-dispersible film forming polymer, based on the total weight of the coating composition; a surfactant present in the coating composition at 0.1% to about 1% on the continuous phase of the coating composition; a polymeric associative thickener present in the coating composition at about 0.1% to about 2% on the continuous phase of the coating composition; about 0.1 wt % to about 5 wt % a styrene acrylic resin, based on the total weight of the coating composition; and an aqueous diluent.

In another aspect, the present disclosure is directed to a coated component including a substrate having thereon a wet coating, the coating including about 5 wt % to about 70 wt % of a latex or a water-dispersible film forming polymer, based on the total weight of the coating composition; a surfactant present in the coating composition at 0.1% to about 1% on the continuous phase of the coating composition; a polymeric associative HEUR thickener present in the coating composition at about 0.1% to about 2% on the continuous phase of the coating composition; about 0.1 wt % to about 5 wt % a low-VOC styrene acrylic resin, based on the total weight of the coating composition; an aqueous diluent; and a pigment.

In another aspect, the present disclosure is directed to a method for coating a component, including applying to a substrate a wet coating composition including about 5 wt % to about 70 wt % of a latex or a water-dispersible film forming polymer, based on the total weight of the coating composition; a surfactant present in the coating composition at 0.1% to about 1% on the continuous phase of the coating composition; a polymeric associative HEUR thickener present in the coating composition at about 0.1% to about 2% on the continuous phase of the coating composition; about 0.1 wt % to about 5 wt % a low-VOC styrene acrylic resin, based on the total weight of the coating composition; an aqueous diluent; and a pigment; and curing the wet coating composition to form a coating on the substrate.

In this application, the recitation of a numerical range using endpoints includes all numbers subsumed within that range (e.g., 1 to 5 includes 1, 1.5, 2, 2.75, 3, 3.80, 4, 5, etc.).

The terms "a," "an," "the," "at least one," and "one or more" are used interchangeably. Thus, for example, a coating composition that contains "an" additive means that the coating composition includes "one or more" additives.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like symbols in the figures indicate like elements.

DETAILED DESCRIPTION

The present disclosure is directed to a waterborne latex coating composition that includes a film forming polymer, a polymeric associative thickener, a polymeric styrene acrylic resin viscosity modifier, a surfactant and water. In this application the term "waterborne" when used in respect to paint, stain or colorant means that the major liquid vehicle or carrier for the paint, stain or colorant is water.

In some embodiments the waterborne latex coating composition is "low VOC," which refers to a coating composition that contains less than about 50 grams/liter volatile organic compounds, more preferably less than about 25 grams/liter volatile organic compounds, and most preferably less than about 5 grams/liter volatile organic compounds based upon the total liquid coating composition. In some embodiments, the waterborne latex coating composition is substantially free of VOCs. When used with respect to a component which may be found in paint, stain or colorant composition, the term "substantially free of" means containing less than about 1 wt % of the component based on the composition weight.

In some embodiments, the polymeric associative thickener and surfactant are present in relative amounts in the waterborne latex coating composition such that the polymeric associative thickener substantially covers the surfaces on the particles of the film-forming polymer to prevent bridge flocculation and maintain the waterborne latex coating composition in the good dispersion region of FIG. 1.

A variety of film forming polymers may be employed in the waterborne latex coating composition, including latex polymers, water-dispersible polymers, water-reducible polymers, and oil-modified polymers. In this application the terms "polymer" and "polymeric" include polymers as well as copolymers of two or more monomers.

Suitable latex polymers for the waterborne latex coating composition include acrylics, (meth)acrylics, vinyls, polyesters, polyurethanes, vinyl acetate ethylene, polybutadiene, polyvinylidene, styrene acrylics, vinyl acrylics, vinyl versatic acid esters, styrene/butadiene, epoxy esters, polysiloxanes, silicones, fluorinated copolymers, and mixtures or copolymers thereof. Such latex polymers normally contain at least polymeric particles, water, and one or more emulsifiers. The waterborne latex polymer particles may include one or more functional groups capable of reacting with an external crosslinker, and such external crosslinker may also be a part of the disclosed compositions. In addition, in some embodiments self-crosslinking functional groups like AAEM (acetoacetoxyethyl methacrylate) may be used.

Suitable latex polymers are typically stabilized using one or more nonionic or anionic emulsifiers (viz., surfactants), used either alone or together. If desired, the latex polymers may be stabilized with an alkali-soluble polymer. A water-soluble free radical initiator is typically used in the polymerization of a latex polymer. The latex polymer may optionally also be functionalized with olefinic groups or other crosslinkable groups where it is desired to enable the latex polymer to participate in radiation curing.

Exemplary commercially available latex polymers include ALBERDINGK AC 2514, ALBERDINGK AC 25142, ALBERDINGK AC 2518, ALBERDINGK AC 2523, ALBERDINGK AC 2524, ALBERDINGK AC 2537, ALBERDINGK AC 25381, ALBERDINGK AC 2544, ALBERDINGK AC 2546, ALBERDINGK MAC 24, and ALBERDINGK MAC 34 polymer dispersions from Alberdingk Boley, Inc.; AQUAMAC 720 from Hexion Specialty Chemicals; EPS 2538 acrylic latex, EPS 2540 styrene acrylic latex and EPS 2725 acrylic latex emulsions from EPS Corp.; vinyl acrylic emulsions available from Celanese Emulsion Polymers under the trade designation RESYN 7305; acrylic emulsions available under the trade designations RHOPLEX 3131-LO, RHOPLEX E-693, RHOPLEX E-940, RHOPLEX E-1011, RHOPLEX E-2780, RHOPLEX HG-95P, RHOPLEX HG-700, RHOPLEX HG-706, RHOPLEX PR-33, RHOPLEX TR-934HS, RHOPLEX TR-3349 and RHOPLEX VSR-1050 from Rohm and Haas Co.;

polymer dispersions available under the trade designations RHO SHIELD 636 and RHO SHIELD 3188 from Rohm and Haas Co.; acrylic emulsions available under the trade designations JONCRYL 538, JONCRYL 1552, JONCRYL 1972, JONCRYL 1980, JONCRYL 1982, JONCRYL 1984 and JONCRYL 8383 from BASF Resins; acrylic latex polymers available under the trade designation NEOCRYL A-1127, NEOCRYL A-6115, NEOCRYL XK-12, NEOCRYL XK-90, NEOCRYL XK-98 and NEOCRYL XK-220 from DSM NeoResins, Inc., and mixtures and combinations thereof.

The waterborne latex compositions may alternatively or optionally contain a water-dispersible or water-reducible polymer. Exemplary water-dispersible polymers include polyurethanes, acrylics, (meth)acrylics, vinyls, polyesters, and mixtures or copolymers thereof. The water-dispersible polymer typically will include as a part of the polymer a group or groups which render the polymer dispersible by itself in water. The water-dispersible polymer may optionally also be functionalized with olefinic groups or other crosslinkable groups where it is desired to enable the water-dispersible polymer to participate in radiation curing.

Exemplary commercially available water-dispersible or water-reducible polymers include acrylic copolymers available from BASF Corporation under the trade designation JONCRYL; PARALOID WR-97 water-reducible acrylic resin from Dow Coating Materials; EPS 6208 water-reducible alkyd resin from Engineered Polymer Solutions, Inc. ("EPS"); ANCAREZ AR555 water-reducible epoxy resin from Air Products and Chemicals, Inc.; BECKOPDX EP386W/56WA water-reducible epoxy resin from Cytec Industries; EPS 3216 water-reducible polyester resin from EPS; EPS 4213 polyurethane dispersion from EPS; BAYHYDROL PR 240 polyurethane dispersion from Bayer Material Science; and POLIDENE vinylidene chloride copolymer emulsions from Scott Bader Inc.

Oil-modified polymers may also be used as latex polymers or if appropriately stabilized as water-dispersible polymers. As used herein, oil-modified polymers include polymers that contain oils or oil based derivatives such as glyceride oils (monoglycerides, diglycerides, and the like), fatty acids, fatty amines, and mixtures thereof. Examples of such oil-modified polymers include alkyds, oil-modified polyurethanes, oil-modified polyamides, oil-modified acrylics, and mixtures or copolymers thereof.

In various embodiments, the waterborne latex coating compositions contain about 1 wt % to about 80% by weight latex or water-dispersible polymer based on the total weight of the non-volatile components in the coating system, about 5 wt % to about 70 wt %, or about 6 wt % to about 65% wt %. If a water-dispersible polymer is also employed, the water-dispersible polymer may be present in an amount less than the amount of latex polymer.

In some embodiments, aqueous emulsions such as acrylics, styrene acrylics, vinyl acrylics and vinyl acetate ethylene have been found to work well in the waterborne latex coating composition. In some embodiments, the polymers and copolymers in these emulsions have a glass transition temperature (Tg) of about −45° C. to about 115° C., and in other embodiments the polymers and copolymers can have glass transition temperatures (Tg) of about 0° C. to about 30° C. In some embodiments, acrylic, and (meth)acrylic monomers can be copolymerized with styrene or vinyl monomers, and may be incorporated into the waterborne latex coating composition in water-borne or 100% solids form. In some embodiments, these resins range in pH from about 1.5 to about 11, or from about 1.7 to about 10, have particle sizes that range from about 30 to about 400 nanometers, and non-volatile matter ("NVM") ranges from about 21% to about 65%.

Examples include, but are not limited to, acrylic aqueous emulsions available from EPS under the trade designations EPS 2103, EPS 2111, EPS 2113, EPS 2117, EPS 2257, EPS 2293, EPS 2705, EPS 2708, EPS 2757 and EPS 2772, as well as styrene acrylic aqueous emulsions EPS 2272, EPS 2507, EPS 2510, EPS 2512, EPS 2514, EPS 2526, EPS 2533, EPS 2535, EPS 2537, EPS 2548, EPS 2550, EPS 2561, EPS 2568, EPS 2572, and EPS 2851.

The waterborne latex coating compositions contain water, which may be tap, deionized, distilled, reverse osmosis or recycled water. Preferably the waterborne latex coating compositions contain sufficient water so that about 20 to about 80 wt % solids and more preferably about 35 to about 65 wt % solids are present when the composition is applied to a substrate.

The waterborne latex coating compositions described herein may also contain one or more cosolvents or plasticizers to assist in mixing or coating the composition; to improve coalescence; to speed up, reduce the required heat or reduce emissions associated with forced drying; or to facilitate air drying. Suitable cosolvents preferably are non-hazardous air pollutant solvents (non-HAPS solvents), may where appropriate be obtained in a water-free (e.g., urethane grade) form, and may for example include glycol ethers (e.g., DOWANOL DPM and from Dow Chemical Co.), M-PYROL N-methyl 2-pyrrolidone from International Specialty Products), the various glycol solvents discussed in International Application No. WO 2008/150294 A1, and mixtures thereof. Texanol ester alcohol from Eastman is very common VOC containing coalescent for latex paint, and other coalescents include Dapro FX 511 from Elementis Specialties, Eastman EEH, Optifilm 300 from Eastman, Dowanol DPnB, and Dowanol PPh.

The waterborne latex coating compositions preferably contain 0 to about 100 and more preferably less than about 30 g/L cosolvent. While not wishing to be bound by any theory, presently available evidence indicates that, in some embodiments, water miscible cosolvents disrupt the water structure and thickener network in the waterborne latex coating composition. In addition, the cosolvents can reduce the adsorption of the polymeric associative thickener molecules on the latex surface and provide more places in the total system for the surfactant to interact, thus mediating the effects of the surfactant. The more hydrophobic the cosolvent, the larger the effect it has on the dispersion characteristics of the thickener/surfactant system.

The waterborne latex coating compositions may optionally include plasticizers such as, for example, CARBOWAX 300 and CARBOWAX 600 polyethylene from Dow Chemical Co., PARAPLEX G-30, PARAPLEX G-41, PARAPLEX G-60, PARAPLEX RGA-2 and PARAPLEX WP-1 from Dow Chemical Co., CITROFLEX 4 citric acid ester from Vertellus Specialties Inc., and mixtures thereof. Low VOC plasticizers include Dapro FX 513, FX 514 from Elementis Specialities, Kflex 500, Kflex 850S from Emerald Performance Materials, Optifilm 400 from Eastman, Loxanol CA5310 and CA5320 from BASF.

In latex paint the level of coalescent or plasticizer is based on factors such as, for example, the Tg of the polymer and on the total weight of latex solids. In some embodiments, which are not intended to be limiting, the coating compositions preferably contain 0 to about 10 wt %, or about 2 to about 5 wt %, plasticizer based on the total composition weight.

The size of the particles of the film forming polymer in the waterborne latex coating composition can vary widely, but the smaller the particle size, the larger the good dispersion region in the phase diagram of FIG. 1. While not wishing to be bound by any theory, presently available evidence indicates that this is due to the increased surface area available for interaction with the thickeners and surfactant in the coating composition. In addition, the CFC (critical flocculation concentration, the lower depletion flocculation region boundary is the critical flocculation concentration below which depletion flocculation will not occur) in the depletion area (FIG. 1) increases with decreasing latex size because at a given volume of solids the smaller the particles of the latex polymer, the smaller the volume from which the soluble polymer is excluded. In some embodiments, which are not intended to be limiting, the film forming polymer particles have a particle size of about 50 nm to about 600 nm, or about 90 nm to about 400 nm, or about 100 nm to about 340 nm.

When a surface of a film forming polymer used in the waterborne latex coating composition is more hydrophilic, as when carboxylic acid based monomers are used, the number of hydrophobic sites available for surfactant and thickeners is reduced. This leads to a smaller bridge flocculation region in FIG. 1 and decreased region of good dispersion due to the small amount of surfactant needed to saturate the latex surface and displace the thickener. When a surface of the film forming polymer used in the waterborne latex coating is more hydrophobic, interactions with the thickener molecules are increased. At the same particle size, the more hydrophobic latex particles tend to have a larger bridge flocculation region in FIG. 3, but also a larger good dispersion region.

In some embodiments, which are not intended to be limiting, preferred film forming polymers include acrylic/methacrylic copolymers with low levels of acrylic or methacrylic acid groups for stability. These acrylic/methacrylic copolymers may optionally include self-crosslinking functionality. Vinyl acrylic, vinyl acetate, vinyl acetate ethylene lattices are more hydrophilic due to the stabilizing moieties, and are less reactive to HEUR associative thickeners.

The waterborne latex coating composition further includes at least one surfactant or dispersant (aside from those which already may be present in the latex polymer). Exemplary surfactants or dispersants include anionic, amphoteric and nonionic materials.

Suitable nonionic surfactants for incorporation into the waterborne latex coating composition include, but are not limited to, compounds of block copolymers based on ethylene oxide and propylene oxide available under the trade designation Pluronic from BASF SE, such as Pluronic L31 (difunctional block copolymer terminating in primary hydroxyl groups), Pluronic 17R2 (difunctional block copolymer terminating in secondary hydroxyl groups), and Pluronic 25R2 (difunctional block copolymer terminating in secondary hydroxyl groups). These compounds have an HLB value of about 1 to about 7. Other suitable surfactants include nonionic octyl and nonyl phenol etholylates from various suppliers with an HLB range from 4 to 18. Linear and secondary alcohol ethoxylates from various suppliers with an HLB range from 4 to 18, as well as other nonionic surfactants like those available from Air Products and Chemicals, Allentown Pa., under the trade designation Carbowet (106, 109, 125, 138, 144, 76) and Surfynol 104 in various solvents like 104BC (butyl Carbitol) 104A (2-ethyl hexanol) 104E (50% in ethylene glycol), 104DPM (dipropylene glycol monomethyl ether), 104H (75% in ethylene glycol), 104PA (isopropyl alcohol), 104PG50 (50% in propylene glycol), Surfynol 440, 465, 485, PSA336, SE, and TG.

Suitable anionic surfactants for incorporation into the waterborne latex coating composition include, but are not limited to, sodium dodecyl sulfate (SDS or NaDS), the Tamol series of polyacid and poly acid copolymer dispersants like Tamol 851, Tamol 1254, Tamol 945, Tamol 1124, Tamol SG-1, Tamol 681, Tamol 731, Tamol 165, from Dow Coating Materials, the Dispex Ultra FA series available from BASF such as Ultra FA 4216, 4204, 4220, 4225, 4231, 4236, 4180 and 4501, the Dispex CX series including Dispex CX 4204, 4340, 4240, 4325, 4910, and 4230, the Dispex AA series including Dispex 4140, 4144, 4030, 4040, the Dispex Ultra PA series including Ultra PA 4500, 4501, 4502, 4503, 4510, 4530, 4550, 4560, 4580, 4585, and 4590, the Dispex Ultra PX series including Ultra PX 4575, the Ecodis series from Coatex (a division of Arkema group) including Ecodis P 30, P 50, and P 90, and the Coadis series including Coadis 123 K, 144A, BR 3, BR 40, and BR 85, as well as Byk 154, and the Disperbyk series including Disperbyk 187, 190, 191, 192, 199, 2010, 2012, and 2015 from Byk Additives and Instruments (division of Altana), and the Rhodoline series from Solvay including Rhodoline 111, 207, 225, 226/35, 230, 231, 270, 286N, and 134.

Other suitable commercially-available surfactants or dispersants include phosphate esters made from octyl phenol or nonyl phenol ethoxylates or tridecyl alcohol ethoxylates reacted with an activated phosphoric acid derivative. Examples include the Strodex and Dextrol phosphate esters from Ashland Aqualon Functional ingredients like the free acid versions Dextrol OC-7525, OC-78N, OC-6025, OC-65K, OC-180, OC-4025, OC-45N, Strodex FT-50K, SEK-50D, TH-100, TH-4427, LFK-70, PSK-28, PK-90, PK-OVOC, MOK-70, KM-OVOC, AND EHK-70. Other suppliers of phosphate esters include Solvay, Dow Chemical, Akzo Nobel, and Huntsman.

In some embodiments, the surfactant or mixture of surfactants in the waterborne latex coating composition should be present at less than about 1% on the continuous phase of the coating composition. In the present application the term "continuous phase" refers to the liquid phase of the waterborne latex coating composition, calculated from the % volatiles in the composition. In some embodiments, the surfactant or mixture of surfactants can be present at about 0.1% to about 1%, or about 0.25% to about 1%, or about 0.3% to about 0.8% on the continuous phase of the coating composition. In some embodiments, the surfactant or mixture of surfactants in the waterborne latex coating composition should be present at about 1 pound per gallon to about 20 pounds per gallon, based on the total weight of the coating composition, or about 2 pounds per gallon to about 12 pounds per gallon, or about 2 pounds per gallon to about 6 pounds per gallon.

The waterborne latex coating composition also contains polymeric associative thickeners and other rheology modifiers. Exemplary polymeric associative thickeners include, but are not limited to, alkali-swellable (or soluble) emulsions (ASEs), nonionic hydrophobically modified ethylene oxide urethane block copolymers (also referred to herein as HEUR thickeners), nonionic hydrophobic ethoxylated aminoplast polymers (referred to herein as HEAT thickeners), and anionic hydrophobically-modified, alkali-soluble or alkali-swellable emulsions (referred to herein as HASE thickeners), and styrene-maleic anhydride terpolymers (SMAT). In the present application the term associative thickener refers to polymeric compounds that associate with or adsorb on the surfaces of the colloidal film forming latex polymer particles in the waterborne latex coating composition using any of molecular bonding, hydrogen bonding, or charge interaction. The associative thickeners interact with themselves and with the latex polymer particles in a system through hydrophobic association, which provides higher viscosities than expected for a given molecular weight of thickener.

In one embodiment, for example, the HEUR thickeners utilize linking molecules such as diisocyanates, polyethers, polyacetals to join with a hydrophobic alcohol such as a polyether polyol to form a substantially linear water-soluble polymeric thickening network. Suitable examples are described in U.S. Pat. Nos. 4,079,028; 4,155,892; 4,426,485; and 5,574,127. In HEAT thickeners, for example, an aminoplast compound is joined with the hydrophobic alcohol and a glycol such as polyethylene glycol (PEG) to provide a thickener with a more branched polymeric structure. Suitable examples include, but are not limited to, associative thickeners available under the trade designation OPTIFLO from Byk-Chemie GmbH, Wesel, Germany.

In various embodiments, the polymeric associative thickeners may be used alone or in combination with non-associative thickeners such as, for example, cellulosics and polysaccharides.

Figure 2:
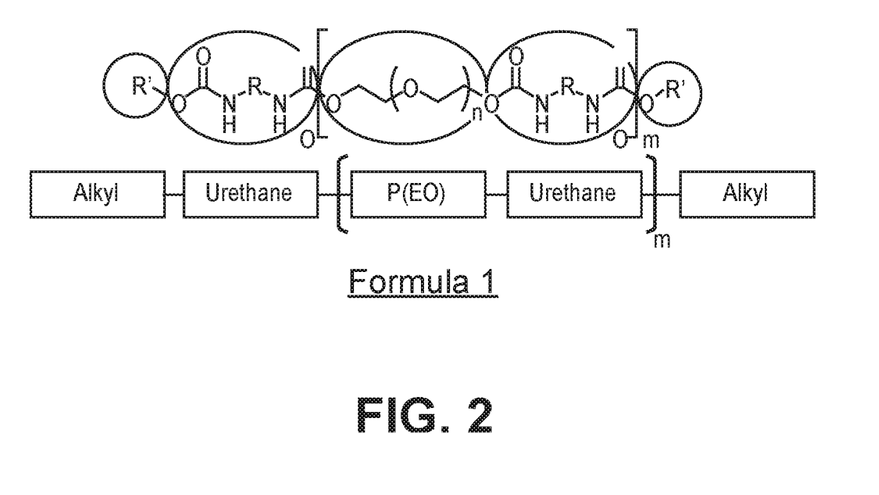
FIG. 2 is a schematic diagram of a HEUR associative thickener.

In some embodiments, which are not intended to be limiting, the waterborne latex coating composition includes the HEUR associative thickener shown diagrammatically in Formula I of FIG. 2.

In some preferred embodiments the HEUR thickeners of Formula I have molecular weights of about 15,000-100,000, and rely almost entirely on association (for example, hydrophobic or ion-dipole adsorption, inter-molecular or intra-molecular self-association, mix micelle formation, and combinations thereof) to build viscosity in the waterborne latex coating composition. In some embodiments the backbone polymers of the HEUR thickeners of Formula I are hydrophobic alcohols such as, for example, PEG poly(ethylene glycol), reacted with diisocynanates (for example, tolune diisocyanate), and the thickeners can be hydrophobically end capped with hydrophobic alcohols or amines if the PEG/NCO adduct is made. In some embodiments, the HEUR thickeners include at least two terminal hydrophobic segments, which can be selected from, for example, polyethers and polyesters.

The performance of the HEUR thickeners of Formula I can be adjusted by varying the ratio of hydrophobic to hydrophilic segments in the molecule, and hydrophobe carbon content can be varied to produce varying hydrophobicity or polyisocyanates and polyols to produce branched or star shaped structures. In some embodiments, hydrophobic groups can be added to the HEUR thickeners of Formula I with copolymerization of EO or with long chain alkyl epoxides. Modification of the copolymers of Formula I can result in changes in thickening efficiency, shear rate dependence of viscosity, and dispersibility.

The presence of hydrophobic and hydrophilic groups in the same HEUR thickener molecule indicates a certain surface activity. Above a certain characteristic concentration, the HEUR thickener molecules tend to form micelles, and the same HEUR thickener molecule may be present in more than one micelle. This results in the formation of structures that reduce the mobility of the water molecules and an increase of the viscosity of the waterborne latex coating composition, which may result in the formation of a gel-like structure. While not wishing to be bound by any theory, the viscosity increase achieved with a HEUR associative thickener is the sum of various physical phenomena such as, for example: increase in the viscosity of the coating composition by dissolution of the HEUR polymer, micelle formation and/or formation of links between HEUR micelles, and association with the surfaces of the film forming polymer particles and any pigment molecules. The links between the HEUR thickener molecules and the particles of the film forming polymer, pigment and solvent can be the result of, for example, any of amide-amide hydrogen bonding, amide-ester bonding, and hydrogen bonding.

Because each HEUR associative thickener molecule contains at least two hydrophobic segments, it is possible for two film forming polymer particles to be linked to one another via the HEUR molecule and to form a skeleton-like structure. The extent to which association takes place with the film forming polymer particles depends on the properties of the hydrophobic group and on the surface properties of the film forming polymer particles. The strength of the structure build-up between the HEUR associative thickener and the film forming polymer particle depends on the strength of the association of the PUR thickener to the dispersion particle surface.

In practice, the strength of the bond depends on the composition of the bonds and the number of the bonds per associated molecule. The quality of the bonds, as far as the thickener molecule is concerned, is influenced by the physical characteristics of the hydrophobic segment. Increasing the hydrophobicity tends to increase the adsorption and as a result increases the viscosity of the waterborne latex coating composition. Regarding the quantity aspect, the number of bonds per film forming polymer molecule is proportional to the thickening effect under high shear conditions.

In some embodiments, the waterborne latex coating composition includes the associative HASE thickeners shown generally in Formula II below:

Formula II

The HASE thickeners of Formula II rely more on their high molecular weight negatively charged backbone to build viscosity than the modes of association utilized by the HEUR thickeners of Formula I. The HASE thickeners of Formula II have molecular weights an order of magnitude higher than the HEUR thickeners of Formula I, and contain enough acid functionality to render them soluble at alkaline pH and have hydrophobes attached to the backbone through ethylene oxide side chains.

In Formula II, the salts of free radical polymers and copolymers of acrylic, methacrylic and maleic acids offer considerable compositional versatility. Molecular weights, choice of comonomer, use of crosslinker, and quantity of hydrophobic group are some of the accessible variables in manipulating the HASE compounds of Formula II for a particular application. For example, hydrophobic groups are can be incorporated directly in the copolymerization as vinyl type monomers, usually with relatively short poly(ethylene oxide) chain between the polymerizable group and the hydrophobe.

In some embodiments, additional thickeners may be used in the waterborne latex coating composition to adjust viscosity. For example, additional thickeners may include Cellulosic thickeners like the CELLOSIZE, METHOCEL, or ETHOCEL line of thickeners from Dow, The Natrosol line of thickeners from Aqualon, and the Bermacol line of thickeners from Akzo Nobel. High shear thickeners for building ICI viscosity include ACRYSOL RM-2020NPR, RM-3000, RM-5000, RM-6000 HEUR Thickeners, and Acrysol RM-7, DR-73, DR-6600, DR-5500 HASE Thickeners commercially available from Dow Chemical Company (Philadelphia, Pa.); Coapur 2020, 2025, 3020, and 3025 HEUR thickeners and Rheotech 2000, 2100, 2800 HASE thickeners from Coatex. For pigment suspension and separation control ATTAGEL attapulgite clay, commercially available from BASF Corporation (Florham Park, N.J.) or BENTONE AD and BENTONE EW both from Elementis Specialties, can be used. In addition, Laponite synthetic magnesium silicate thickeners from Byk and Lattice NTC (microcrystalline cellulose & sodium carboxymethyl cellulose) from FMC BioPolymer can be used.

The HASE thickeners of Formula II differ from HEUR thickeners of Formula I in that the HASE thickeners have a much higher molecular weight, are ionic, and have a lower hydrophobe density (hydrophobe number per molecular volume). As a result, in some embodiments HASE systems can be more easily depletion flocculated than HEUR systems due partially by weaker associations with the film forming polymer particles.

The thickener or mixture of thickeners in the waterborne latex coating composition should be present at about 0.1% to about 2%, or about 0.2% to about 1.5%, or about 0.3% to about 1%, or about 0.5% to about 0.8% on the continuous phase of the coating composition. In the present application the term "continuous phase" refers to the liquid phase of the waterborne latex coating composition, calculated from the % volatiles in the composition.

The latex waterborne coating composition further includes a styrene acrylic resin that can aid in film formation while reducing the viscosity of the waterborne latex coating composition without adding additional surfactants or VOCs to the composition. While not wishing to be bound by any theory, presently available evidence indicates that the styrene acrylic resin lowers the KU viscosity which allows more polymeric associative thickener to be used in the composition, which can reduce or substantially eliminate bridge flocculation. Increasing the amount of thickener in the composition allows the thickener to more completely coat the surfaces of the particles of the film forming polymer and optional pigment particles to prevent bridge flocculation and move the coating composition into the good dispersion region of FIG. 1. Addition of surfactant can move the coating composition into the depletion flocculation region of FIG. 1, and can result in a coating having less desirable performance. While not wishing to be bound by any theory, the polymeric styrene acrylic resin can behave like a surfactant in reducing the KU viscosity of the waterborne coating composition without causing the problems resulting from addition of low molecular weight surfactants, which can move the coating composition into the depletion flocculation region of FIG. 1. In addition, the added surfactant can contribute to water sensitivity, stain resistance and lower scrub resistance.

Suitable styrene acrylic resins should be dispersible in a coating composition that includes the latex film forming polymers described herein, and facilitate film formation at temperatures of less than about 25° C., and even at temperatures of 5 to 10° C. Preferred styrene acrylic resins have a VOC content of less than about 50%, preferably less than about 30%, more preferably, less than about 20%, and most preferably, less than about 15%.

Exemplary suitable styrene acrylic polymers include, but are not limited to, JONCRYL 63, JONCRYL 67, JONCRYL 678, JONCRYL ECO 694 (all available from BASF), NEOCRYL BT-100 OR BT-175 (available from DSM Neoresins), MOREZ 101 (available from Rohm and Haas), CARBOSET GP-1166, GA-2299, OR GA-2300 (available from Noveon), EASTACRYL Emulsion 30D (available from Eastman Chemical Co.), SECRYL 35 (available from Omnova Solutions) and VANCRYL 65 or 68 (available from Cytec Surface Specialities).

The styrene acrylic resins are present in the waterborne latex coating compositions at about 0.1 to about 5 wt % and more preferably about 0.5 to about 2 wt %, or about 0.8 to about 1.5 wt %, or about 1 to about 1.2 wt %, based on total composition weight.

In various embodiments, the waterborne latex coating composition may also include a wide range of additives including, but not limited to, dispersants, fire retarders, water absorbers, water repellants, mold inhibitors, UV light resistant compounds, pH adjusters, rheology modifiers, flow control agents, defoamers, and the like.

For example, defoamers may include multi-hydrophobe blend defoamers and other defoamers known to those of ordinary skill in the art. For example, suitable defoamers may include FOAMASTER, commercially available from BASF Corporation and TEGO FOAMEX 810 from Evonik).

In some embodiments, the waterborne latex coating composition may include fillers such as, for example, inorganic mineral fillers such as sodium-potassium alumina silicates, microcrystalline silica, talc (magnesium silicate), and other fillers known to those of ordinary skill in the art. For example, fillers may include MINEX 7, commercially available from the Cary Company (Addison, Ill.); IMSIL A-10, commercially available from the Cary Company; and TALCRON MP 44-26, commercially available from Specialty Minerals Inc. (Dillon, Mont.).

In some embodiments, the waterborne latex coating composition may include an in-can preservative or biocide including, but not limited to, broad-spectrum microbicides that prohibit bacteria and fungi growth, antimicrobials such as those based on the active diiodomethyl-ptolylsulfone, AMICAL Flowable, commercially available from Dow Chemical Company, and other compounds known to those of ordinary skill in the art. For example, biocides may include KATHON LX 1.5%, commercially available from Dow Chemical Company, 1,2-benzisothiazolin-3-one (BIT), 5-chloro-2-methyl-4-isothiazolin-3-one/2-methyl-4-isothiazolin-3-one (CMIT/MIT) or Kathon LX 1.5%, 2-methyl-4-isothiazolin-3-one (MIT), 2,2-dibromo-3-nitrilopropionamide (DBNPA), 1-(3-chloroallyl)-3,5,7-triaza-1-azoniaadamantane chloride (CTAC, DOWICIL 75), Dimethylol-dimethyl-hydantoin (DMDMH), 1,2-dibromo-2,4-dicyano-butane (DBDCB), Zinc pyrithione (ZPT), and N-methyl-1,2-benzisothiazol-3(2H)-one (MBIT).

Biocides may also act as preservatives. Commonly used dry paint film biocides can be classified according to their microbial spectrum. In other words, they can be classified based on whether their major activity is fungicidal or algaecidal or both. Typical fungicides used in the paint industry for dry film preservation include: carbendazim (BCM), chlorothalonil (CTL), iodopropynylbutylcarbamate (IPBC), octylisothiazolinone (OIT), dichlorooctylisothiazolinone (DCOIT), n-butyl-benzisothiazolinone (BBIT), and zinc pyrithione (ZnPT). Prevention of fungal defacement is typically the focus of paint formulation biocide programs, however algal growth can be a significant problem as well. Most paint film fungicides are not good algaecides, however zinc pyrithione has anti-algal activity as well as anti-fungal activity. POLYPHASE 663, commercially available from Troy Corporation (Newark, N.J.), and BUSAN1292 from Buckman Laboratories, Inc., and NOPCOCIDE N-40D from Cognis are examples of these.

In some embodiments, the waterborne latex coating composition may include a UV absorber such, as for example, encapsulated hydroxyphenyl-triazine compositions and other compounds known to those of ordinary skill in the art, for example, TINUVIN from Ciba Specialty Chemicals, and EVERSORB 80 from Everlight Chemical.

These additives are optionally present in the waterborne latex coating composition up to about 5 wt %, or at about 0.01 wt % to about 2 wt %, or about 0.1 wt % to about 1 wt %, based on the total weight of the composition.

In some embodiments, the waterborne latex coating composition include a "colorant," which in this application means a composition that may be added to alter the hue or lightness of the composition, and which contains pigment or dye and an optional vehicle but is substantially free of film forming polymeric components.

In some embodiments, the waterborne latex coating composition includes a pigment, which in this application refers not only to particulate pigments that function by reflecting light but also soluble or dispersible dyes that function by absorbing light.

In various embodiments, suitable examples of pigments include, without limitation, titanium dioxide white, carbon black, lamp black, black iron oxide, red iron oxide, yellow iron oxide, brown iron oxide (a blend of yellow and red oxide with black oxide), phthalocyanine green, phthalocyanine blue, organic reds (such as naphthol red, quinacridone red and toluidine red), quinacridone magenta, quinacridone violent, DNA orange, and/or organic yellows (such as Hansa yellow), for example.

In various embodiments, the pigment volume concentration in the waterborne latex coating composition can vary from about 0 wt % for a high gloss clear base to over about 40 wt % for low quality flat white paint, or from about 0 wt % to about 30 wt %, or from about 1 wt % to about 25 wt %. The term "pigment volume concentration" when used in respect to a paint, stain or colorant means the total percentage of dried coating volume occupied by all pigment species in the coating.

The coating compositions may contain a variety of other adjuvants that will be familiar to persons having ordinary skill in the art. Representative adjuvants are described in Koleske et al., Paint and Coatings Industry, April, 2003, pages 12-86. Exemplary adjuvants and commercial examples of the same include anti-cratering agents, biocides (e.g., coalescents, curing indicators, fillers, flatting agents (e.g., talcs, silicas, silicates and wollastonites such as VAN-SIL fillers from R. T. Vanderbilt), insulating fillers such as ZEEOSPHERES ceramic microspheres from Zeeospheres Ceramics, LLC, heat stabilizers, leveling agents, light stabilizers (e.g., hindered amine light stabilizers such as TINUVINT 123-DW and TINUVIN 292 HP from Ciba Specialty Chemicals), mildewcides, optical brighteners, plasticizers, preservatives (e.g., KATHON LX from Rohm & Haas), waxes (e.g., AQUACER 593 from Altana, HYDROCER 303 from Shamrock Technologies, Inc. and MICHEM Emulsion 32535 from Michelman, Inc.), wetting agents (e.g., BYK 346 and BYK 348 from Altana, and TROYSOL LAC from Troy corporation), and the like. The types and amounts of these and other adjuvants typically will be empirically selected for use with the particular application and curing equipment at a given manufacturing site, and with the adjuvant being added to the disclosed first part, second part or to both the first and second parts.

In an embodiment, the waterborne latex coating composition described herein is suitable for use in a low-VOC or zero-VOC coating composition, paint, or stain to be colored or tinted to a desired color and finish, such as an in-store tintable base paint, for example. In this application the term "stain" means a coating composition including a film forming polymer that, when applied to form a thin (e.g., 100 µm) wet thickness coating film on a freshly-sanded smooth wood surface, will when dried not hide both the wood grain and its texture. When a semi-transparent stain is applied to wood, the wood grain and its texture normally both remain noticeable, whereas when a solid color (viz., opaque) stain is applied the grain normally becomes hidden while the texture normally remains noticeable. A stain typically will soak into a wood or other porous substrate to a much greater extent than will a paint.

Some embodiments of the waterborne latex coating composition described herein are suitable for use as a "topcoat," which in this application refers to a coating composition which when dried or otherwise hardened provides a decorative or protective outermost finish layer on a coated substrate. By way of further explanation, such topcoats may be applied in one or more layers and may be applied to bare or primer-coated substrates.

Some embodiments of the waterborne latex coating composition described herein are suitable for use as a "primer," which in this application refers to a coating composition that is applied in one or more layers to a bare substrate and which if left uncoated without a topcoat would not be capable of withstanding extended outdoor exposure (e.g., exposure equivalent to one year of vertical south-facing Florida sunlight) without visually objectionable deterioration.

The coating compositions may be applied to a variety of substrates including thermoplastic, thermoplastic composite or thermoplastic-clad materials, as well as to other materials including thermoset, thermoset composite, thermoset-clad, wood, impregnated wood, wood-derived and metal materials. In some embodiments, the waterborne latex coating composition may be used as an "architectural paint" or "architectural stain," which respectively refer to paints and stains for use on interior or exterior building components.

The coating compositions may be applied using a variety of methods that will be familiar to persons having ordinary skill in the art, including spraying (e.g., air-assisted, airless or electrostatic spraying), brushing, roller coating, flood coating and dipping. The compositions may be applied at a variety of wet film thicknesses.

Preferably the wet film thickness is such as to provide a dry film thickness of about 13 to about 260 μm (about 0.5 to about 10 mil) and more preferably about 25 to about 75 μm (about 1 to about 3 mil) for the cured coating. The applied coating may be cured by allowing it to air dry or by accelerating curing using a variety of drying devices (e.g., ovens) that will be familiar to persons having ordinary skill in the art. Preferred heating temperatures for curing the coating compositions are about 50° C. to about 65° C., and more preferably about 60° C. to about 65° C., and preferred heating times are at least three minutes and less than 60 minutes, less than 45 minutes, less than 30 minutes, less than 15 minutes, less than 10 minutes, less than six minutes or less than five minutes. The heating time will tend to decrease with increased temperature, increased airflow or decreased humidity.

Paints made using the waterborne latex coating composition described herein provide excellent block, scrub, stain, and early water resistance.

In some embodiments, paints made with the waterborne latex coating composition described herein demonstrate excellent block resistance. Block resistance is measured by a standard test as described below, and block ratings are assigned on a scale from 0 to 10, where a rating of 0 corresponds to very poor block resistance, and a rating of 10 corresponds to excellent block resistance. In an aspect, the paints described herein show 1-day and 7-day block ratings of preferably at least 6, more preferably at least 7, and most preferably at least 8.

In some embodiments, paints made with the waterborne latex coating composition described herein demonstrate superior scrub resistance. Scrub resistance is measured by a standard test as described below. The film is cured for seven (7) days, and scrub resistance is reported as a number of scrubs applied before the film failed, i.e. scrubbed off the substrate surface. In an aspect, the paints described herein display scrub resistance of at least about 600 scrubs, more preferably about 800 to 1300, and most preferably about 900 to 1200.

The invention is illustrated by the following examples. It is to be understood that the particular examples, materials, amounts, and procedures are to be interpreted broadly in accordance with the scope and spirit of the inventions as set forth herein. Unless otherwise indicated, all parts and percentages are by weight and all molecular weights are weight average molecular weight. Unless otherwise specified, all chemicals used are commercially available from, for example, Sigma-Aldrich, St. Louis, Mo.

EXAMPLES

The components used in the examples are listed in Table 1 below:

TABLE 1

| Component | Description | Available from |
|---|---|---|
| VSR1050 | Acrylic emulsion | DOW |
| WQ2218P | Precomposite Latex | EPS |
| Kronos 4310 | TiO2 Slurry | Kronos |
| Optifilm OT1200 | Open time additive | Eastman Chemical |
| Joncryl 63 | Styrene Acrylic Resin | BASF |
| Tamol 731 | Dispersant | DOW |
| Coadis 123K | Dispersant | Coatex |
| Kronos 2310 | Dry TiO2 | Kronos |
| NHS-310 | HEUR High Shear Thickener | Aqualon |
| XLS-525 | HEUR Low Shear Thickener | Aqualon |

The KU viscosity was measured by a Brookfield KU-2 viscometer.

The ICI viscosity was measured by a BYK CAP 1000+L viscometer.

The gloss was measured by BYK Gardner micro-TRI-gloss meter.

Example 1

OT 1200, an open-time promoter, JONCRYL 67 styrene acrylic polymer, and tri(ethylene glycol) bis(2-ethylhexanoate) (TEG-EH), were evaluated to determine their effect on KU viscosity. As shown in Table 2 below, Joncryl 67 (as Joncryl 63, the 33% solution of Joncryl 67) was found to be most effective in producing KU reduction.

TABLE 2

Took the finished trial batch with out any OT1200 in it split into pints and made the following post adds %
HEUR on Continuous phase 0.56%

|  | A | B | C | D | E |
|---|---|---|---|---|---|
| Satin Pastel Base A | 600 | 600 | 600 | 600 | 600 |
| OT1200 | 0 | 5 | 0 | 0 | 0 |
| Joncryl 63 | 0 | 0 | 8.46 | 0 | 0 |
| TEG-EH | 0 | 0 | 0 | 1.08 | 0 |
| CHDM | 0 | 0 | 0 | 0 | 3.4 |
| Initial KU | 102.5 | 91.5 | 93.4 | 102.1 | 98.5 |
| ICI | 1.033 | 0.804 | 0.867 | 1.078 | 1.012 |
| Sag | 24+ | 12 | 14 | 24+ | 24+ |
| F&L | 5 | 9 | 9 | 5 | 6 |
| 3 mil C/R | A/X | 98.83/98.54 | 98.80/98.46 | 98.77/98.40 | 98.72/98.47 |

Joncryl 63 is the neutralized 30.5% solids low VOC version of Joncryl 67 which is a solid flake. It has a typical VOC of 0.4% wt
Joncryl 67 is a styrene acrylic solid flake resin, MW 13,000, Tg 73'C typical VOC 1.4% wt Example 2

Further work showed that paints with enough HEUR thickener to not be bridge flocculated did not show a significant response to additions of OT1200. As shown in Table 3 below, when the paint was not in the bridge flocculated region of the dispersion phase diagram, neither OT1200 or Joncryl 63 caused a reduction of KU viscosity.

TABLE 3

Took treatment 7 from PF006 DOE split it into ½ pints and made the following post adds

| | | | | |
|---|---|---|---|---|
| Evoque 1140 | 333 | | 37.88396 | 8.79 |
| VSR1050 | 99 | | 11.25 | 8.80 |
| Kronos 4310 TiO2 slurry | 333 | | 17.38903 | 19.15 |
| Tamol 731 dispersant | 4.6 | | 0.5 | 9.20 |
| Extender | 20 | | 1.091107 | 18.33 |
| Ninate 411 surfactant | 2 | | 0.235294 | 8.50 |
| Add to Mixing Letdown | | | | |
| NHS-310 HEUR thickener | 30 | | 3.464203 | 8.66 |
| MIX 15 MIN | | | | |
| Acrysol RM-825 HEUR Thickener | 5.2 | | 0.597701 | 8.70 |
| TOTAL WT | 826.80 | | 72.4113 | |
| TOTAL VOL | 100.00 | | | |
| THEO WT./GAL | 8.27 | | | |
| % HEUR Actives on Continuous Phase | 1.33% | | | |

| amt per ½ pt | T7e | 299.80 | 299.80 | 299.80 | 299.80 | 299.80 |
|---|---|---|---|---|---|---|
| | | A | B | C | D | |
| | OT1200 | 0 | 5 | 0 | 0 | 0 |
| | Joncryl 63 | 0 | 0 | 4.23 | 0 | 0 |
| | TEG-EH | 0 | 0 | 0 | 0.53 | 0 |
| | CHDM | 0 | 0 | 0 | 0 | 1.7 |
| | KU | 106.6 | 118.1 | 118.6 | 107.4 | 102.7 |
| | ICI | 1.129 | 0.608 | 0.684 | 1.129 | 1.042 |

Example 3

Ladder studies of OT1200 were done in the satin pastel base A that was bridge flocculated to see how small increments of OT1200 influenced the low shear viscosity.

The results for the ladder study of OT1200 are shown in Table 4 below.

TABLE 4

Satin Pastel Base A

| OT1200# | 0 | 2 | 4 | 6 | 8 | 10 |
|---|---|---|---|---|---|---|
| Letdown | A | B | C | D | E | F |
| VSR1050 | 185 | | | | | |
| Evoque 1140 | 259 | | | | | |
| Kronos 4310 TiO2 slurry | 345 | | | | | |
| Coadis 123K dispersant | 9 | | | | | |
| Triton X-405 | 2 | | | | | |
| Extender | 65 | | | | | |
| ADD TO MIXING LETDOWN | | | | | | |
| Acrysol RM3000 HEUR Thickener | 14 | | | | | |
| MIX 5 MIN | | | | | | |
| Acrysol RM-845 HEUR Thickener | 0.4 | | | | | |
| MIX 20 MIN | | | | | | |
| Eastman Optifilm OT1200 | 0 | 2 | 4 | 6 | 8 | 10 |
| % HEUR active on Continuous phase | 0.56% | 0.56% | 0.56% | 0.56% | 0.56% | 0.56% |
| % OT1200 solids on continuous phase | 0 | 0.25% | 0.49% | 0.74% | 0.99% | 1.23% |
| TOTAL WT | 1092.43 | 1092.58 | 1092.73 | 1092.88 | 1093.03 | 1093.17 |
| TOTAL VOL | 100.00 | 100.00 | 100.00 | 100.00 | 100.00 | 100.00 |
| WT/GAL | 10.92 | 10.93 | 10.93 | 10.93 | 10.93 | 10.93 |
| | A | B | C | D | E | F |
| initial KU | 95.8 | 94 | 92.3 | 90.9 | 89.6 | 88.7 |
| ICI | 1.312 | 1.196 | 1.121 | 1.121 | 1.129 | 1.083 |
| o/n KU | 100.6 | 99.4 | 98.4 | 97.2 | 96.5 | 96 |
| ICI | 1.546 | 1.183 | 1.117 | 1.096 | 1.021 | 1.05 |
| sag | 24 | 20 | 18 | 16 | 16 | 16 |
| F&L | 4.17 | 7.33 | 8.67 | 9.00 | 9.00 | 9.50 |
| 60' gloss | 18.8 | 18.9 | 19.3 | 19.6 | 20.3 | 20.8 |

TABLE 4-continued

| Satin Pastel Base A | | | | | | | |
|---|---|---|---|---|---|---|---|
| 80' gloss | | 37.8 | 39 | 40.8 | 41.1 | 42.3 | 42.1 |
| 120 F. syneresis mm | overnight | 3 mm | 1 mm | very slight | almost none | N/A | N/A |
| 120 F. syneresis mm | 1 wk | 5 mm | 4 mm | 3.5 mm | 3 mm | 2 mm | 1 mm |

As shown in Table 4, sample A has 0.56% HEUR active solids on continuous phase and from the dispersion phase diagram in FIG. 1, there was a good possibility that the paint was bridge flocculated. This assumption was supported by the fact that sample A had the worst flow and leveling and the most sag resistance, and developed 3 mm of syneresis overnight.

Additions of OT1200 in 2 pound increments gradually caused the overnight syneresis to go away and the sag to go down and flow and leveling to go up.

FIG. 2 is a collection of flow sweep curves of Satin Pastel Base A, which showed the influence low levels of OT1200 have on low shear viscosity, which influenced sag resistance and flow and leveling. About 6 pounds OT1200 was enough to move the paint formula out of the bridge flocculated region and improve syneresis and flow and leveling.

Example 4

Ladder studies of JONCRYL 63 were done in the satin pastel base A that was bridge flocculated to see how small increments of JONCRYL 63 influenced the low shear viscosity. The results for the ladder study of JONCRYL 63 are shown in Table 5 below.

Similar to the OT1200 evaluated in Example 3, JONCRYL 63 (the 30.5% solids pre-neutralized solution of JONCRYL 67) showed a reduction in KU viscosity with a decrease in sag, increase in flow and leveling and reduction in overnight syneresis.

Figure 3:
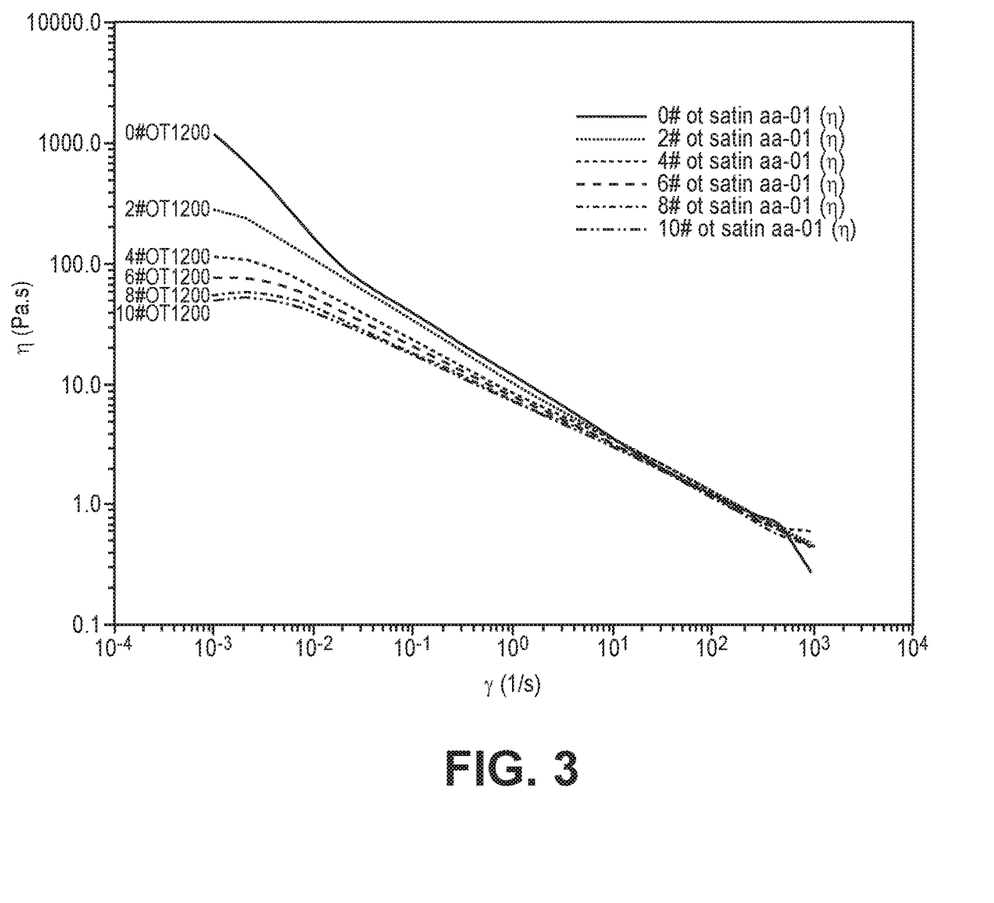
FIG. 3 is a set of flow sweep curves of Satin Pastel Base A with OT1200 from Example 3.
Figure 4:
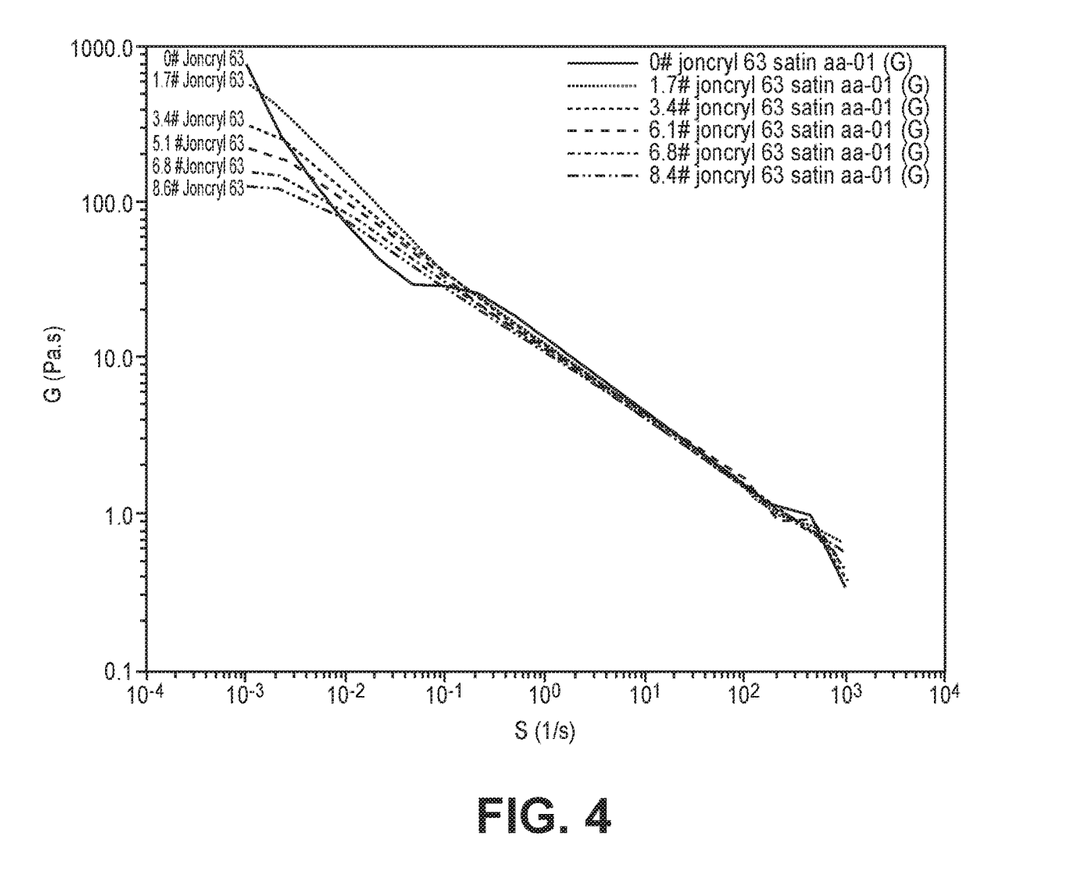
FIG. 4 is a set of flow sweep curves of Satin Pastel Base A with JONCRYL 63 from Example 4.

FIG. 3 depicts flow sweep curves of Satin Pastel Base A, which show the influence low levels of JONCRYL 63 have on low shear viscosity, which influenced sag resistance and flow and leveling.

Example 5

Similar post adds to the bridge flocculated satin pastel Base A were made with Ninate 411, an alkyl aryl sulfonate surfactant, which behaves similarly to sodium dodecyl sulfate in moving a paint system out of the bridge flocculated region. This surfactant is very efficient in suppressing the KU viscosity of associative thickened systems.

The results are shown in Table 6 below.

TABLE 5

| Satin Pastel Base A | | | | | | |
|---|---|---|---|---|---|---|
| Joncryl 63# | 0 | 1.7 | 3.4 | 5.1 | 6.8 | 8.46 |
| | A | B | C | D | E | F |
| VSR1050 | 185 | | | | | |
| Evoque 1140 | 259 | | | | | |
| Kronos 4310 TiO2 slurry | 345 | | | | | |
| Coadis 123K | 9 | | | | | |
| Triton X-405 | 2 | | | | | |
| extender | 65 | | | | | |
| ADD TO MIXING LETDOWN | | | | | | |
| Acrysol RM3000 HEUR Thickener | 14 | | | | | |
| MIX 5 MIN | | | | | | |
| Acrysol RM-845 HEUR Thickener | 0.4 | | | | | |
| MIX 20 MIN | | | | | | |
| Joncryl 63 | 0 | 1.7 | 3.4 | 5.1 | 6.8 | 8.46 |
| % HEUR active on Continuous phase | 0.56% | 0.56% | 0.56% | 0.56% | 0.56% | 0.56% |
| % Joncryl 63 solids on continuous phase | 0 | 0.1 | 0.2 | 0.3 | 0.4 | 0.5 |
| TOTAL WT | 1092.43 | 1092.526 | 1092.626 | 1092.826 | 1092.926 | 1093.086 |
| TOTAL VOL | 100.00 | 100 | 100 | 100 | 100 | 100 |
| WT/GAL | 10.92 | 10.93 | 10.93 | 10.93 | 10.93 | 10.93 |
| | A | B | C | D | E | F |
| initial KU | | 99.1 | 97.9 | 97.3 | 97 | 96.1 | 94.1 |
| ICI | | 1.258 | 1.179 | 1.125 | 1.117 | 1.096 | 1.100 |
| o/n KU | | 105.4 | 105 | 104.9 | 104.6 | 104.3 | 103.8 |
| ICI | | 1.454 | 1.208 | 1.279 | 1.196 | 1.142 | 1.167 |
| sag | | 24 | 24 | 22 | 20 | 20 | 20 |
| F&L | | 3.83 | 5.00 | 6.00 | 6.50 | 6.67 | 7.67 |
| 60' gloss | | 17.9 | 17.8 | 18.1 | 18.2 | 17.5 | 18.6 |
| 80' gloss | | 35.8 | 36.5 | 37.6 | 37.9 | 37.8 | 38.2 |
| 120 F. syneresis mm | overnight | 4 mm | 3 mm | 2 mm | Less than 1 mm | very slight | N/A |
| 120 F. syneresis mm | 1 wk | 6 mm | 5.5 mm | 3 mm | 3 mm | 2 mm | Less than 1 mm |

TABLE 6

| Satin Pastel Base A | | | | | |
|---|---|---|---|---|---|
| Ninate 411# | 0 | 2 | 4 | 6 | 8 |
| VSR1050 | 185 | | | | |
| WQ0393B | 63.75 | | | | |
| Evoque 1140 | 259 | | | | |
| Kronos 4310 TiO2 slurry | 345 | | | | |
| Coadis 123K | 9 | | | | |
| Extender | 65 | | | | |
| Triton X-405 | 2 | | | | |
| ADD TO MIXING LETDOWN | | | | | |
| Acrysol RM3000 HEUR Thickener | 14 | | | | |
| MIX 5 MIN | | | | | |
| Acrysol RM-845 HEUR Thickener | 0.4 | | | | |
| MIX 20 MIN | | | | | |
| Ninate 411 | | 0 | 2 | 4 | 6 | 8 |
| TOTAL WT | | 1092.03 | 1092.03 | 1092.08 | 1092.13 | 1092.18 |
| TOTAL VOL | | 100.00 | 100.00 | 100.00 | 100.00 | 100.00 |
| WT/GAL | | 10.92 | 10.92 | 10.92 | 10.92 | 10.92 |
| initial KU | | 100.7 | 95 | 86.1 | 78.4 | 73.6 |
| ICI | | 1.229 | 1.137 | 0.975 | 0.846 | 0.737 |
| o/n KU | | 105.8 | 102.4 | 95.6 | 90.2 | 88.7 |
| ICI | | 1.258 | 1.171 | 1.033 | 0.858 | 0.804 |
| sag | | 24 | 22 | 16 | 14 | 14 |
| F&L | | 3.33 | 5.67 | 8.67 | 8.83 | 8.83 |
| 60' gloss | | 17.4 | 18.5 | 19.2 | 19.5 | 19.7 |
| 80' gloss | | 35.9 | 37.8 | 39.3 | 40.2 | 40.6 |
| 120 F. syneresis mm | overnight | 5 mm | 2 mm | N/A | N/A | N/A |
| 120 F. syneresis mm | 1 wk | 5 mm | 4 mm | very slight, unmeasurable | N/A | N/A |

As low as 4 pounds per gallon Ninate 411 dropped the KU viscosity from 100.7 KU's to 86 KU's, eliminated overnight syneresis and improves the Flow and Leveling. This solution would require much more additional thickener to bring the viscosity back into specification.

EMBODIMENTS

A. A coating composition including about 5 wt % to about 70 wt % of a latex or a water-dispersible film forming polymer, based on the total weight of the coating composition; a surfactant present in the coating composition at 0.1% to about 1% on the continuous phase of the coating composition; a polymeric associative thickener present in the coating composition at about 0.1% to about 2% on the continuous phase of the coating composition; about 0.1 wt % to about 5 wt % a styrene acrylic resin, based on the total weight of the coating composition; and an aqueous diluent.
B. The composition of embodiment A, wherein the polymeric associative thickener is chosen from HEUR thickeners, HASE thickeners, and combinations thereof.
C. The composition of embodiments A-B, wherein the polymeric associate thickener is a HEUR thickener.
D. The composition of any of embodiments A-C, wherein the HEUR thickener includes a backbone including poly(ethylene glycol) (PEG) or diisocyanate.
E. The composition of any of embodiments A-D, wherein the HEUR thickener comprises end caps on the backbone, and wherein the end caps are chosen from hydrophobic alcohols, hydrophobic amines, and combinations thereof.
F. The composition of any of embodiments A-E, wherein the HEUR thickener has a molecular weight of about 15,000 to about 100,000.
G. The composition of any of embodiments A-F, wherein the styrene acrylic resin has a VOC concentration of less than about 50%.
H. The composition of any of embodiments A-G, wherein the film forming polymer includes a (meth)acrylic polymer.
I. The composition of any of embodiments A-H, wherein the surfactant includes at least one of nonionic octylphenol ethoxylates and sodium dodecyl sulfate.
J. The composition of any of embodiments A-I, wherein the aqueous diluent includes a cosolvent.
K. The composition of any of embodiments A-J, wherein the coating composition further includes a colorant.
L. The composition of embodiment K, wherein the colorant includes a pigment.
M. A coated component comprising a substrate having thereon a wet coating, the coating including about 5 wt % to about 70 wt % of a latex or a water-dispersible film forming polymer, based on the total weight of the coating composition; a surfactant present in the coating composition at 0.1% to about 1% on the continuous phase of the coating composition; a polymeric associative HEUR thickener present in the coating composition at about 0.1% to about 2% on the continuous phase of the coating composition; about 0.1 wt % to about 5 wt % a low-VOC styrene acrylic resin, based on the total weight of the coating composition; an aqueous diluent; and a pigment.
N. The component of embodiment M, wherein the HEUR thickener has backbone including poly(ethylene glycol) (PEG) or diisocyanate and end caps on the backbone, and wherein the end caps are chosen from hydrophobic alcohols, hydrophobic amines, and combinations thereof.
O. The component of any of embodiments M-N, wherein the HEUR thickener has a molecular weight of about 15,000 to about 100,000.
P. The component of any of embodiments M-0, wherein the film forming polymer includes a (meth)acrylic polymer.
Q. The component of any of embodiments M-P, wherein the surfactant includes at least one of nonionic octylphenol ethoxylates and sodium dodecyl sulfate.

R. A method for coating a component, including applying to a substrate a wet coating composition including: about 5 wt % to about 70 wt % of a latex or a water-dispersible film forming polymer, based on the total weight of the coating composition; a surfactant present in the coating composition at 0.1% to about 1% on the continuous phase of the coating composition; a polymeric associative HEUR thickener present in the coating composition at about 0.1% to about 2% on the continuous phase of the coating composition; about 0.1 wt % to about 5 wt % a low-VOC styrene acrylic resin, based on the total weight of the coating composition; an aqueous diluent; and a pigment; and curing the wet coating composition to form a coating on the substrate.

Various embodiments of the invention have been described. These and other embodiments are within the scope of the following claims.

The invention claimed is:

1. A coating composition, comprising:
   about 5 wt % to about 70 wt % of a latex or a water-dispersible film forming polymer, based on the total weight of the coating composition;
   a surfactant present in the coating composition at 0.1% to about 1% on the continuous phase of the coating composition;
   a polymeric associative thickener present in the coating composition at about 0.1% to about 2% on the continuous phase of the coating composition;
   about 0.1 wt % to about 1.5 wt % of a styrene acrylic resin, based on the total weight of the coating composition; and
   an aqueous diluent.

2. The composition of claim 1, wherein the polymeric associative thickener is chosen from HEUR thickeners, HASE thickeners, and combinations thereof.

3. The composition of claim 2, wherein the polymeric associate thickener is a HEUR thickener.

4. The composition of claim 3, wherein the HEUR thickener comprises a backbone comprising poly(ethylene glycol) (PEG) or diisocyanate.

5. The composition of claim 4, wherein the HEUR thickener comprises end caps on the backbone, and wherein the end caps are chosen from hydrophobic alcohols, hydrophobic amines, and combinations thereof.

6. The composition of claim 5, wherein the HEUR thickener has a molecular weight of about 15,000 to about 100,000.

7. The composition of claim 1, wherein the styrene acrylic resin has a VOC concentration of less than about 50%.

8. The composition of claim 1, wherein the film forming polymer comprises a (meth)acrylic polymer.

9. The composition of claim 1, wherein the surfactant comprises at least one of nonionic octylphenol ethoxylates and sodium dodecyl sulfate.

10. The composition of claim 1, wherein the aqueous diluent comprises a cosolvent.

11. The composition of claim 1, wherein the coating composition further comprises a colorant.

12. The composition of claim 11, wherein the colorant comprises a pigment.

13. A coated component comprising a substrate having thereon a wet coating, the coating comprising:
   about 5 wt % to about 70 wt % of a latex or a water-dispersible film forming polymer, based on the total weight of the coating composition;
   a surfactant present in the coating composition at 0.1% to about 1% on the continuous phase of the coating composition;
   a polymeric associative HEUR thickener present in the coating composition at about 0.1% to about 2% on the continuous phase of the coating composition;
   about 0.1 wt % to about 1.5 wt % of a low-VOC styrene acrylic resin, based on the total weight of the coating composition;
   an aqueous diluent; and
   a pigment.

14. The component of claim 13, wherein the HEUR thickener has backbone comprising poly(ethylene glycol) (PEG) or diisocyanate and end caps on the backbone, and wherein the end caps are chosen from hydrophobic alcohols, hydrophobic amines, and combinations thereof.

15. The component of claim 13, wherein the HEUR thickener has a molecular weight of about 15,000 to about 100,000.

16. The component of claim 13, wherein the film forming polymer comprises a (meth)acrylic polymer.

17. The component of claim 13, wherein the surfactant comprises at least one of nonionic octylphenol ethoxylates and sodium dodecyl sulfate.

18. A method for coating a component, comprising:
   applying to a substrate a wet coating composition comprising:
      about 5 wt % to about 70 wt % of a latex or a water-dispersible film forming polymer, based on the total weight of the coating composition;
      a surfactant present in the coating composition at 0.1% to about 1% on the continuous phase of the coating composition;
      a polymeric associative HEUR thickener present in the coating composition at about 0.1% to about 2% on the continuous phase of the coating composition;
      about 0.1 wt % to about 1.5 wt % of a low-VOC styrene acrylic resin, based on the total weight of the coating composition;
      an aqueous diluent; and
      a pigment; and
   curing the wet coating composition to form a coating on the substrate.

* * * * *